(12) United States Patent
Fu et al.

(10) Patent No.: US 12,350,520 B1
(45) Date of Patent: Jul. 8, 2025

(54) RADIOTHERAPY SYSTEM BASED ON MULTI-ISOCENTER

(71) Applicant: JIANGSU RAYER MEDICAL TECHNOLOGY CO., LTD, Wuxi (CN)

(72) Inventors: Dongshan Fu, Wuxi (CN); Lujun An, Wuxi (CN); Zhenyu Gu, Wuxi (CN); Shanda Ma, Wuxi (CN)

(73) Assignee: JIANGSU RAYER MEDICAL TECHNOLOGY CO. LTD., Wuxi (CN)

( * ) Notice: Subject to any disclaimer, the term of this patent is extended or adjusted under 35 U.S.C. 154(b) by 0 days.

(21) Appl. No.: 19/121,084

(22) PCT Filed: May 31, 2024

(86) PCT No.: PCT/CN2024/096728
§ 371 (c)(1),
(2) Date: Apr. 14, 2025

(87) PCT Pub. No.: WO2024/260238
PCT Pub. Date: Dec. 26, 2024

(30) Foreign Application Priority Data

Jun. 20, 2023 (CN) .......................... 202310739652.6

(51) Int. Cl.
*A61N 5/10* (2006.01)
(52) U.S. Cl.
CPC .......... *A61N 5/1049* (2013.01); *A61N 5/1075* (2013.01); *A61N 5/1083* (2013.01); *A61N 2005/1061* (2013.01)
(58) Field of Classification Search
None
See application file for complete search history.

(56) References Cited

U.S. PATENT DOCUMENTS

| 11,679,281 | B1 * | 6/2023 | Schnarr | ................ | A61N 5/1049 378/62 |
| 2007/0189455 | A1 | 8/2007 | Allison | | |

(Continued)

FOREIGN PATENT DOCUMENTS

| CN | 101015723 A | 8/2007 |
| CN | 101238351 A | 8/2008 |

(Continued)

OTHER PUBLICATIONS

Internation Search Report for PCT/CN2024/096728 dated Jul. 16, 2024.

(Continued)

*Primary Examiner* — Hoon K Song
(74) *Attorney, Agent, or Firm* — MOSER TABOADA

(57) ABSTRACT

A radiotherapy system based on multi-isocenter includes an accelerator and a three-sequence image-guided positioning system. The three-sequence image-guided positioning system includes multiple low-level image-guided positioning systems corresponding to a low-level treatment center and a high-level image-guided positioning system corresponding to a high-level treatment center. The high-level image-guided positioning system is arranged among the multiple low-level image-guided positioning systems. The intersection of two beams generated by any two image-guided positioning systems among the low-level image-guided positioning systems and the high-level image-guided positioning system is the low-level treatment center. A beam generated by the high-level image-guided positioning system passes through the high-level treatment center. Multiple treatment nodes with the low-level treatment center as a spherical center and multiple treatment nodes with the high-level treatment center as a spherical center form a fully-spherical treatment space.

9 Claims, 10 Drawing Sheets

(56) References Cited

U.S. PATENT DOCUMENTS

| | | | |
|---|---|---|---|
| 2008/0123813 A1 | 5/2008 | Maurer et al. | |
| 2009/0213990 A1 | 8/2009 | Bergfjord | |
| 2010/0104068 A1* | 4/2010 | Kilby | A61N 5/1031 |
| | | | 378/65 |
| 2018/0028839 A1* | 2/2018 | Yoshimizu | A61N 5/1065 |
| 2019/0380666 A1 | 12/2019 | Sheng et al. | |
| 2020/0170598 A1* | 6/2020 | Shea | A61B 6/542 |
| 2022/0305292 A1* | 9/2022 | Harper | A61N 5/1084 |

FOREIGN PATENT DOCUMENTS

| | | |
|---|---|---|
| CN | 102222331 B | 9/2013 |
| CN | 107567343 A | 1/2018 |
| CN | 113491844 A | 10/2021 |
| CN | 215841267 U | 2/2022 |
| CN | 116803449 A | 9/2023 |
| WO | WO 2023/005902 A1 | 2/2023 |

OTHER PUBLICATIONS

Chinese Office Action for Application No. 202310739652.6 dated Dec. 21, 2023.

* cited by examiner

RADIOTHERAPY SYSTEM BASED ON MULTI-ISOCENTER

CROSS-REFERENCE TO RELATED APPLICATION(S)

This is a national stage application filed under 35 U.S.C. 371 based on International Patent Application No. PCT/CN2024/096728, filed May 31, 2024, which claims priority to Chinese Patent Application No. 202310739652.6 filed with the China National Intellectual Property Administration (CNIPA) on Jun. 20, 2023, the disclosure of which are incorporated herein by reference in their entireties.

TECHNICAL FIELD

The present application relates to the technical field of a radiosurgery robot, for example, to a radiotherapy system based on multi-isocenter.

BACKGROUND

The radiosurgery robot system is a special device for radiosurgery therapy, and is mainly used for precise radiotherapy of solid tumors of the whole body. The radiosurgery robot system based on a multi-degree-of-freedom robot requires an ideal fully-spherical treatment space so that the treatment beam from an accelerator can be projected to the patient's target volume from different positions and different directions of the sphere to achieve the optimal treatment dose distribution and obtain the best treatment effect. The treatment center of the radiosurgery system is the reference point for the entire system. A sphere is defined with this treatment center as the center of the sphere, and multiple (up to thousands) nodes evenly distributed on the sphere are planned, and are called fully-spherical treatment nodes. The set of all treatment nodes on the sphere is the fully-spherical treatment space. A treatment planning system selects optimized treatment nodes (tens to hundreds) for specific patients from the fully-spherical treatment space to meet the clinical requirements for optimal dose distribution. In Patent CN113491844B, a fully-spherical radiotherapy system projects beams to the target volume near the dorsum, such as a spinal target volume and the chest and abdominal target volumes near the dorsum, through a treatment space of the high-level treatment center, so that the patient can receive effective treatment in a normal supine position; and the fully-spherical treatment space combining a low-level treatment center and a high-level treatment center is used to allow each target volume to receive more treatment beam projections, obtain a more optimized and more effective treatment dose distribution, and achieve better treatment results. However, when the system is in the low-level treatment center mode, some treatment nodes may be blocked and the two-sequence imaging system corresponding to the low-level treatment center may be blocked by the treatment head, resulting in the inability to position very accurately.

SUMMARY

The technical problem to be solved by this application is to overcome poor positioning effect caused by imaging of part of the treatment space being blocked and the limited treatment space of the radiosurgery robot system in the related art, and provide a radiotherapy system based on multi-isocenter, which realizes radiosurgery treatment on the fully-spherical treatment space through three-sequence image-guided two treatment spaces respectively composed of the low-level treatment center and the high-level treatment center.

A radiotherapy system based on multi-isocenter is provided according to the present application, which includes an accelerator and a three-sequence image-guided positioning system.

The three-sequence image-guided positioning system includes multiple low-level image-guided positioning systems corresponding to a low-level treatment center and a high-level image-guided positioning system corresponding to a high-level treatment center. The high-level image-guided positioning system is arranged among the multiple low-level image-guided positioning systems.

The low-level treatment center is located at an intersection of two beams generated by any two image-guided positioning systems of the multiple low-level image-guided positioning systems and the high-level image-guided positioning system. A beam generated by the high-level image-guided positioning system passes through the high-level treatment center. Multiple treatment nodes with the low-level treatment center as the spherical center and multiple treatment nodes with the high-level treatment center as the spherical center form a fully-spherical treatment space.

Optionally, the radiotherapy system further includes a multi-degree-of-freedom robot. The accelerator is arranged on the multi-degree-of-freedom robot. The multi-degree-of-freedom robot carrying the accelerator forms at least one of a treatment space of the low-level treatment center above and on both sides of a patient around the low-level treatment center, or a treatment space of the high-level treatment center below and on both sides of a patient around the high-level treatment center.

Optionally, the multiple low-level image-guided positioning systems and the high-level image-guided positioning system each include a ray source and a ray detector.

Optionally, the low-level treatment center and the high-level treatment center meet the following conditions:

$$3000 \text{ mm} \leq d_{11} + d_{12} \leq 3800 \text{ mm} \tag{1}$$

$$0.69 \leq h_1/d_{11} \leq 0.72 \tag{2}$$

$$3000 \text{ mm} \leq d_{21} + d_{22} \leq 3500 \text{ mm} \tag{3}$$

$$0.72 \leq h_2/d_{21} \leq 0.98 \tag{4}$$

$$0.42 \leq (h_2 - h_1)/h_1 \leq 0.56 \tag{5}$$

In the above conditions, $d_{11}$ is the distance from the low-level treatment center to an imaging center of a ray detector corresponding to the low-level treatment center; $d_{12}$ is the distance from the low-level treatment center to a ray source of a low-level image-guided positioning system; $d_{21}$ is the distance from the high-level treatment center to the ray detector of the high-level image-guided positioning system; $d_{22}$ is the distance from the high-level treatment center to the ray source of the high-level image-guided positioning system; $h_1$ is the height of the low-level treatment center from the ground; and $h_2$ is the height of the high-level treatment center from the ground.

Optionally, a distance H1 from the ray source of the low-level image-guided positioning system to the ground is $H_1 = h_1 + \cos(\alpha) d_{12}$, where $\alpha$ is an included angle between a beam of the low-level image-guided positioning system and a vertical plane with respect to the ground.

Optionally, a distance $H_2$ from the ray source of the high-level image-guided positioning system to the ground is $H_2=h_2+d_{22}$.

Optionally, an included angle between a beam of the low-level image-guided positioning system and the vertical plane with respect to the ground is α, $α=\arccos(d_{11}/(h_1+d))$, where d is the distance from a ray detector of a low-level image-guided positioning system to the ground.

Optionally, the ray source is an X-ray tube; and the ray detector is a flat-panel detector.

Optionally, the radiotherapy system further includes an adjustment and calibration device; and the ray detector is connected to the adjustment and calibration device.

Optionally, the adjustment and calibration device includes a height adjustment mechanism, a plane longitudinal adjustment mechanism, and a plane lateral adjustment mechanism.

BRIEF DESCRIPTION OF DRAWINGS

The drawings are only intended to illustrate embodiments and are not intended to limit the present application.

DETAILED DESCRIPTION

The present application is described below in conjunction with the drawings and embodiments. In the absence of conflict, the embodiments of the present application and the features in the embodiments can be combined with each other. In addition, the present application can also be implemented in other ways different from those described herein, so the scope of protection of the present application is not limited by the embodiments disclosed below.

Figure 1:
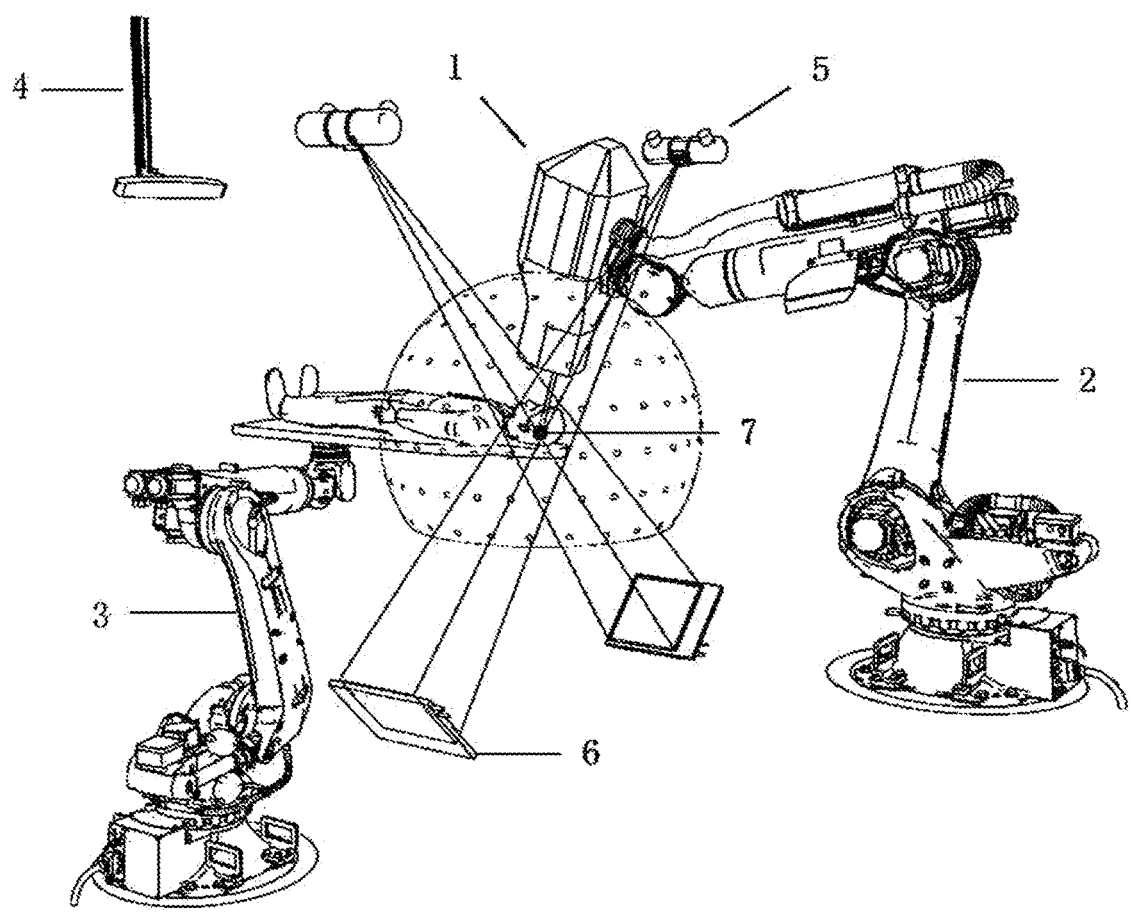
FIG. 1 is a schematic diagram of a radiosurgery robot system according to the present application.
Figure 2:
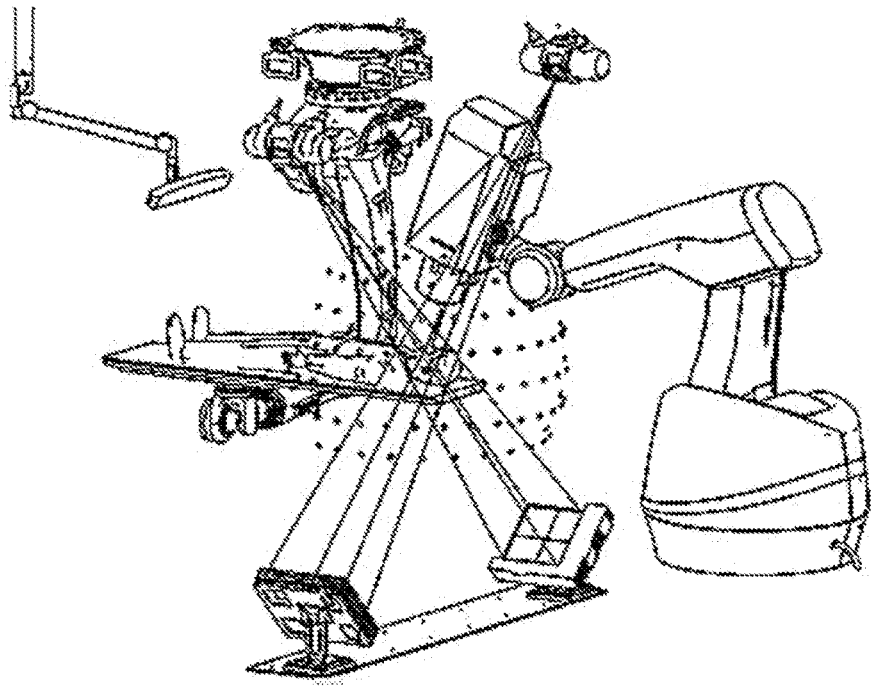
FIG. 2 is a schematic diagram of treatment performed by the radiotherapy device adopting a low-level treatment center treatment mode according to the present application.
Figure 3:
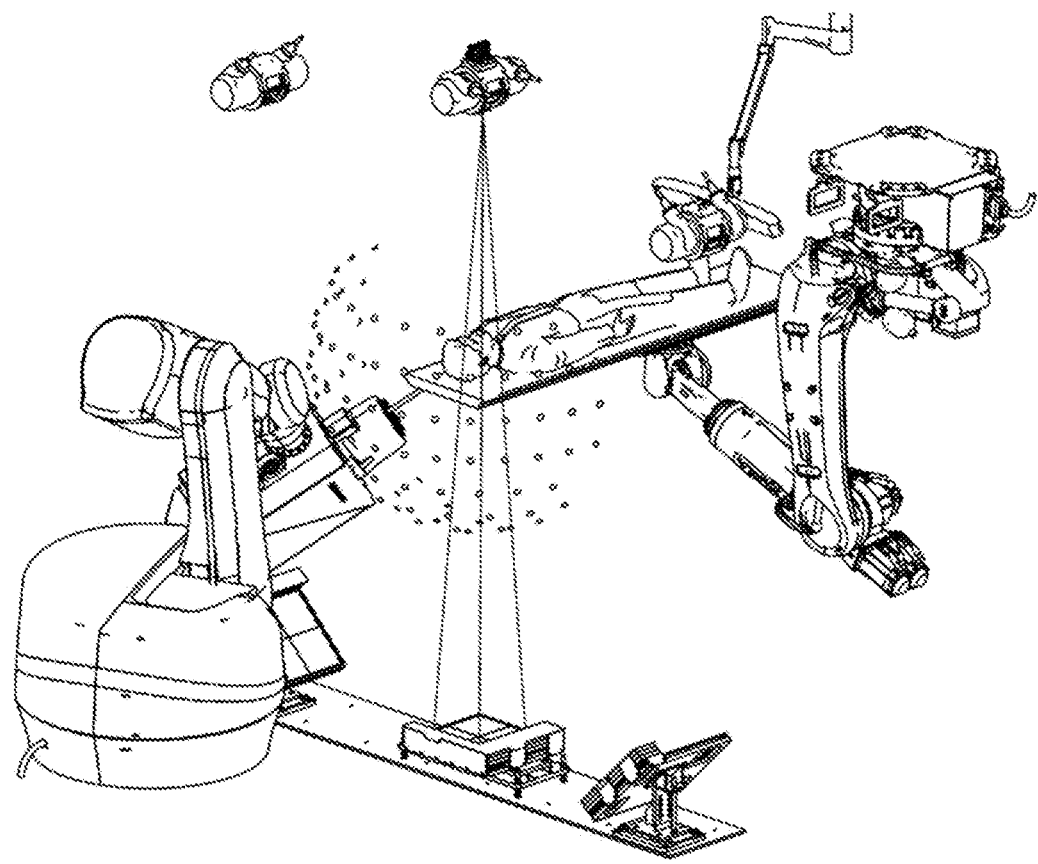
FIG. 3 is a schematic diagram of treatment performed by the radiotherapy device adopting a high-level treatment center treatment mode according to the present application.

In an embodiment of the present application, a radiotherapy system based on multi-isocenter is disclosed, and its structural composition is as shown in FIG. 2 and FIG. 3. The radiotherapy system based on multi-isocenter includes a miniaturized linear accelerator 1, a six-degree-of-freedom robot 2 equipped carrying the accelerator, a six-degree-of-freedom robot treatment couch 3, a respiratory motion tracking system 4 and a three-sequence image-guided positioning system.

The respiratory motion tracking system 4 uses infrared optical motion tracking technology to detect body surface motion in real time, and combines the image-guided positioning system to achieve real-time motion tracking of the target volume in the body.

The three-sequence image-guided positioning system includes a low-level image-guided positioning system 5 corresponding to a low-level treatment center 7 and a high-level image-guided positioning system corresponding to a high-level treatment center 8. Two low-level image-guided positioning systems 5 are provided, and one high-level image-guided positioning system is provided.

Figure 4:
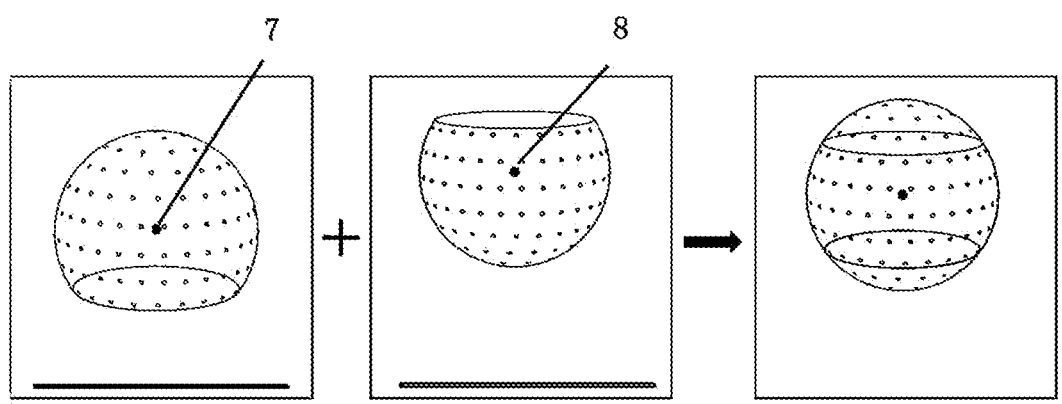
FIG. 4 is a schematic diagram showing the combination of the low-level treatment center treatment mode and high-level treatment center treatment mode used by the radiotherapy device according to the present application.

The imaging hardware of the three-sequence image-guided positioning system is composed of: three X-ray tubes, three high-voltage generators (generally disposed between devices) corresponding to the three X-ray tubes, and three X-ray flat-panel detectors. One high-voltage generator is connected to one X-ray tube and is configured to provide high voltage to the X-ray tube. The low-level image-guided positioning system takes the low-level treatment center 7 as the imaging center, and the imaging hardware composition of the low-level image-guided positioning system is as shown in FIG. 2, a first X-ray tube 51 and a second flat-panel detector 62 produce an X-ray image on a projection plane, and a second X-ray tube 52 and a first flat-panel detector 61 produce an X-ray image on another projection plane. The high-level image-guided positioning system takes the high-level treatment center 8 as the imaging center, and the imaging hardware composition of the high-level image-guided positioning system is as shown in FIG. 3, a third X-ray tube 53 and a third flat-panel detector 63 produce an X-ray image on a projection plane. As shown in FIG. 4, a treatment space of the low-level treatment center is defined above and on two sides of the patient around the low-level treatment center 7, and a treatment space of the high-level treatment center is defined below and on two sides of the patient around the high-level treatment center 8. The combination of the treatment space of the low-level treatment center and treatment space of the high-level treatment center provides a fully-spherical treatment space.

Figure 5A:
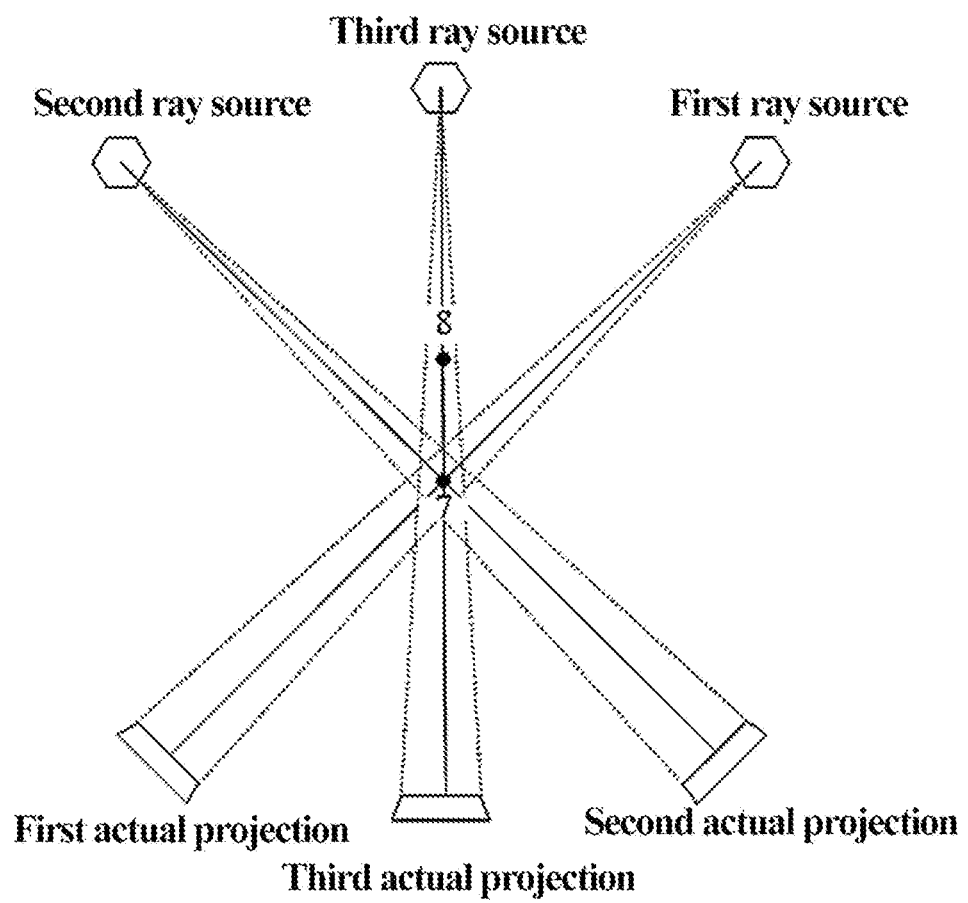
FIG. 5A is a schematic diagram showing imaging geometry of the radiotherapy device according to the present application.

In the imaging geometry of the image-guided positioning system of the radiotherapy system based on multi-isocenter, as shown in FIG. 5A, each of a first ray source, a second ray source and a third ray source (i.e., the first X-ray tube 51, the second X-ray tube 52 and the third X-ray tube 53) emit a ray beam separately, and three ray beams intersects to obtain a location of the low-level treatment center 7, and generate a first actual projection, a second actual projection and a third actual projection on three flat-panel detectors (i.e., the first flat-panel detector 61, the second flat-panel detector 62 and the third flat-panel detector 63); after calibration, the third ray source emits a beam, and the beam passes through the high-level treatment center 8, and generates a third actual projection on the third flat-panel detector 63.

Mounting positions of multiple components of the radiotherapy system and the adaptation relationships between the multiple components are key parameters and design priorities of the technical solution of the present application. The height of the low-level treatment center 7, the height of the high-level treatment center 8 and the relative height between the low-level treatment center and the high-level treatment center need to be designed due to the limitation imposed by the height of ceiling from the ground and the requirements for ensuring image quality. The distance from the center of a bulb tube source of an X-ray tube to the flat-panel imaging center of the flat-panel detector also greatly affects the imaging quality.

Moreover, it is necessary to consider the influence of the source-axis distance (SAD), the treatment couch stroke and components such as the ray source center of the accelerator. Under the conditions of ensuring no collision between hardware, no collision between hardware and the ground and no collision between hardware and the treatment safe zone, the six-degree-of-freedom mechanical arm of the six-degree-of-freedom robot 2, carrying the accelerator, should be capable of reaching as many spatial positions as possible above, below and on two sides of the patient. Therefore, it is necessary to perform overall design and verification in consideration of the preceding mounting conditions.

Figure 5B:
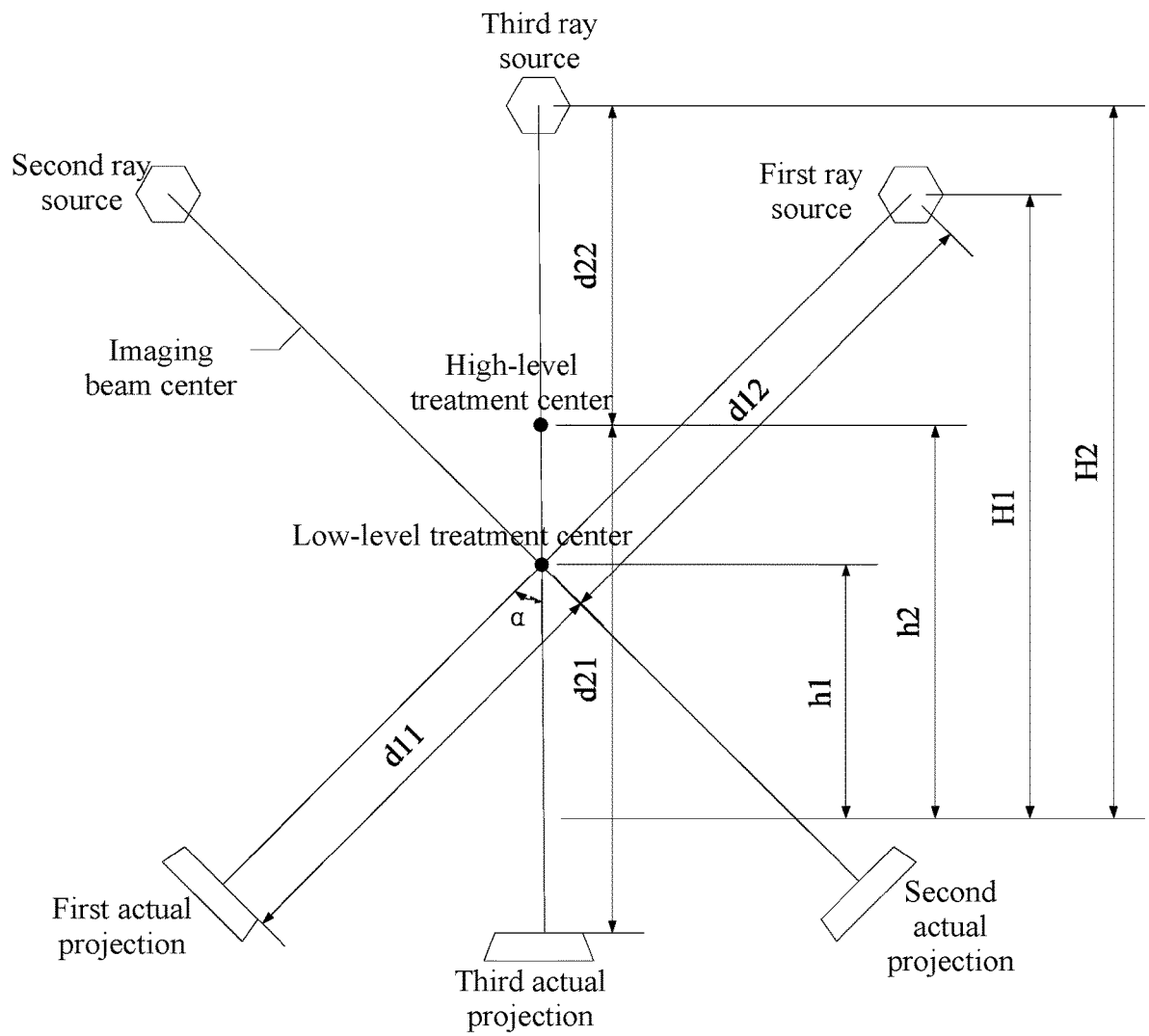
FIG. 5B is another schematic diagram showing imaging geometry of the radiotherapy device according to the present application.

Based on the preceding considerations, the present application performs theoretical calculation on position relationships between multiple components and performs design according to the results, and performs simulation and practical verification on the design scheme so as to achieve the convenience of various practical operations during the treatment and satisfy the balance requirements for the imaging quality under various conditions. Referring to the structure and multiple parameters shown in FIG. 5B, the low-level treatment center and the high-level treatment center meet the following conditions:

$$3000 \text{ mm} \leq d_{11} + d_{12} \leq 3800 \text{ mm} \tag{1}$$

$$0.69 \leq h_1/d_{11} \leq 0.72 \tag{2}$$

$$3000 \text{ mm} \leq d_{21} + d_{22} \leq 3500 \text{ mm} \tag{3}$$

$$0.72 \leq h_2/d_{21} \leq 0.98 \tag{4}$$

$$0.42 \leq (h_2 - h_1)/h_1 \leq 0.56 \tag{5}$$

In the above conditions, $d_{11}$ is the distance from the low-level treatment center 7 to an imaging center of a corresponding flat-panel detector (i.e., the first flat-panel detector 61 and the second flat-panel detector 62); $d_{12}$ is the distance from the low-level treatment center 7 to the center of the bulb tube source of the X-ray tube of the low-level image-guided positioning system (i.e., the first X-ray tube 51 and the second X-ray tube 52); $d_{21}$ is the distance from the high-level treatment center 8 to the imaging center of the flat-panel detector (i.e., the third flat-panel detector 63); $d_{22}$ is the distance from the high-level treatment center 8 to the center of the bulb tube source of the X-ray tube (i.e., the third X-ray tube 53) of the high-level image-guided positioning system; $h_1$ is the height from the low-level treatment center 7 to the ground; $h_2$ is the height from the high-level treatment center 8 to the ground.

Furthermore, in the technical solution of the present application, in addition to satisfying all the installation conditions of the above formulas (1)-(5), the following conditions further need to be satisfied: the distance $H_1$ between the X-ray tube of the image-guided system of the low-level treatment center and the ground is $H_1 = h_1 + \cos(\alpha) \cdot d_{12}$, optionally, the value range of $H_1$ is from 2200 mm to 2400 mm, the distance $H_2$ from the X-ray tube of the image-guided system of the high-level treatment center to the ground is $H_2 = h_2 + d_{22}$, optionally, the value range of $H_2$ is from 2800 mm to 3000 mm; the range of the angle $\alpha$ between the beam center of the low-level treatment center and the vertical plane with respect to the ground is $\alpha = \arccos(d_{11}/(h_1+d))$, d is the distance from the upper edge of the third flat-panel detector 63 to the ground, $d = d_{21} - h_2$, so that no matter in the low-level treatment center or the high-level treatment center, the accelerator and the six-degree-of-freedom mechanical arm of the six-degree-of-freedom robot 2 will not block the imaging path, and moreover, good imaging quality and effect can be ensured, where $\alpha$ can be selected as ranging from 0° to 60°, and d can be selected as ranging from 10 mm to 50 mm.

Figure 11:
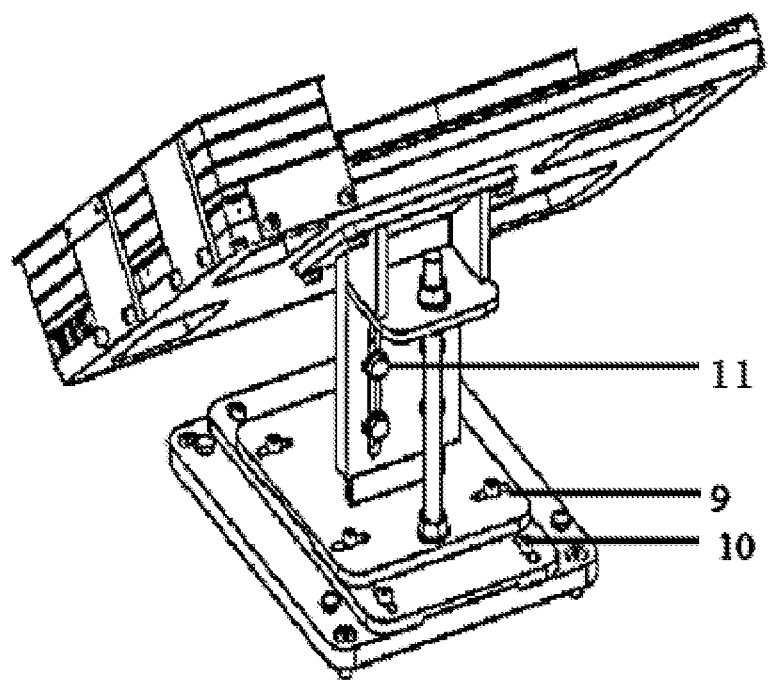
FIG. 11 is a schematic diagram of a flat-panel detector and an adjustment and calibration device of a radiotherapy device according to the present application.

As shown in FIG. 11, the flat-panel detector is connected to the adjustment and calibration device. The adjustment and calibration device includes a height adjustment mechanism 11, a plane longitudinal adjustment mechanism 9 (reciprocating axially along the length of the six-degree-of-freedom robot treatment couch), a plane lateral adjustment mechanism 10 (reciprocating perpendicular to the direction of the reciprocating movement of the plane longitudinal adjustment mechanism 9) and an angle adjustment mechanism (not shown in the drawings). The flat-panel detector is adjusted and calibrated in three directions and tilt angle by the adjustment and calibration device.

The height adjustment mechanism 11 includes a lifting screw rod, a support plate, a connecting plate and a lifting plate. The lifting plate is sleeved on the support plate, the lifting plate is provided with two first strip-shaped grooves, multiple bolts are arranged on the support plate at positions corresponding to the first strip-shaped grooves, and the multiple bolts are arranged from top to bottom in the height direction. The connecting plate is arranged at the top of the lifting plate and the lifting screw rod, so that the lifting screw rod plays a guiding and fixing role in adjusting height of the flat-panel detector. Two lateral sides of the support plate are provided with guide rails, and two lateral sides of the lifting plate are provided with guide strips matching the guide rails.

The plane longitudinal adjustment mechanism 9 includes a first flat plate, and the plane lateral adjustment mechanism 10 includes a second flat plate. The bottom of the support plate and the bottom of the lifting screw rod are both arranged on an upper surface of the first flat plate. The first flat plate is axially provided with multiple second strip-shaped grooves along the length of the six-degree-of-freedom robot treatment couch, and a bolt is arranged on the second flat plate at the position corresponding to each second strip-shaped groove. The adjustment and calibration device further includes a bottom plate, the second flat plate is provided with multiple third strip-shaped grooves in a horizontal plane direction perpendicular to the second strip-shaped grooves, and a bolt is arranged on the bottom plate at the position corresponding to each third strip-shaped groove.

The bottom of the flat-panel detector is connected to the top of the height adjustment mechanism 11, an angle adjustment mechanism is provided at the connection, and the angle of the flat-panel detector is adjusted by the angle adjustment mechanism.

After the flat-panel detector is adjusted and calibrated, the positions of the three ray sources (the first X-ray tube 51, the second X-ray tube 52 and the third X-ray tube 53) and the three flat-panel detectors are fixed, that is, the positions of the low-level treatment center 7 and the high-level treatment center 8 are fixed. In the process of treatment, it is only necessary to lift and lower the treatment couch to the low-level treatment center 7 or the high-level treatment center 8 according to the treatment requirements.

During the treatment at the low-level treatment center, based on the different node positions of the treatment head mechanical arm, carrying the accelerator, of the six-degree-of-freedom robot 2, there is a situation where the treatment head mechanical arm blocks an imaging path, thus, it is possible to use any two imaging sequences that do not block any imaging path in the three-sequence image guidance system, for positioning, and image-guided positioning can be performed throughout the treatment process to achieve better treatment effects.

The beam emitted by the X-ray ray source of the low-level image-guided positioning system is perpendicular to the actual projection plane of the flat-panel detector so that an orthographically projected X-ray image is generated, and for the two-dimensional/three-dimensional image registration method of an X-ray image and a computed tomography (CT) image for image-guided positioning, reference may be made to the two-dimensional/three-dimensional medical image registration method and system based on two flat panels in the Patent No. ZL201110125385.0

The high-level image-guided positioning system adopts the middle vertical single-sequence image-guided positioning, and the imaging quality is higher.

The beams emitted by the ray sources of the low-level image-guided positioning systems and the high-level image-guided positioning system are perpendicular to the actual projection surfaces of the flat-panel detectors, to generate orthographic X-ray images.

When the three-sequence image-guided positioning system is at the low-level treatment center 7, two unblocked beams are selected for image-guided positioning.

When the three-sequence image-guided positioning system switches from the low-level treatment center 7 to the high-level treatment center 8, the treatment couch needs to be raised by a distance of $h_2-h_1$. While the treatment couch is controlled to rise, the position change $\Delta d$ of an infrared marker preset on the treatment couch is monitored by using the respiratory motion tracking system 4 to satisfy: $\Delta d=h_2-h_1$, so as to ensure accurate switching from the low-level treatment center 7 to the high-level treatment center 8.

Figure 7:
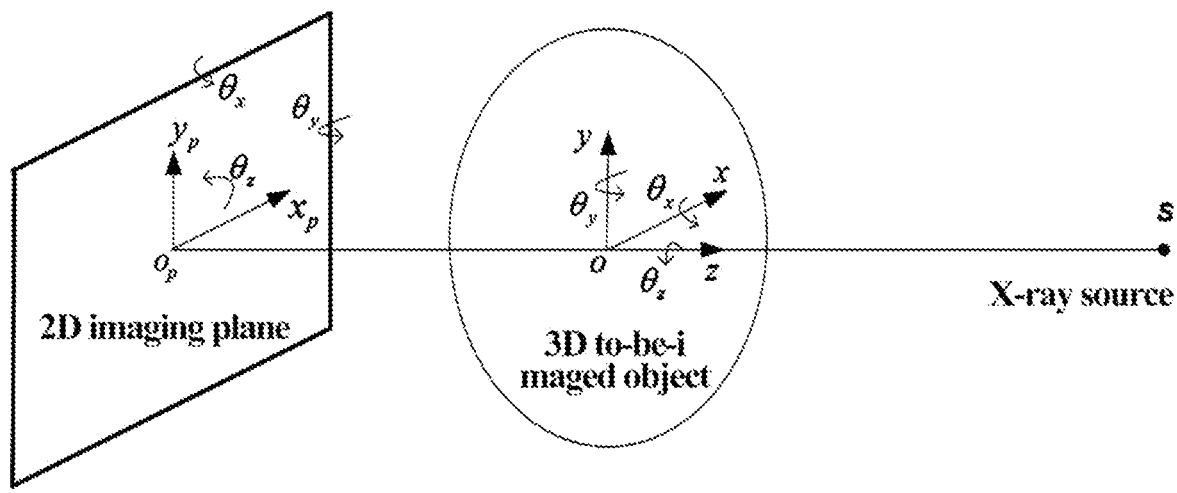
FIG. 7 is a coordinate diagram of the radiotherapy device when using only the beam of the middle sequence for single sequence image-guided positioning and registration according to the present application.

When the three-sequence image-guided positioning system is at the high-level treatment center 8, only the beam of the middle sequence (i.e., emitted by the third ray source) is used for single-sequence image-guided positioning and registration. As shown in FIG. 7, S, O and $o_p$ represent the center of the third ray source, the patient center and the center of the imaging plane (i.e., the third actual projection), respectively. The three-dimensional patient coordinate system (oxyz) is the patient coordinate system, and the patient position is described by six degrees of freedom, including three translations (x, y, z) and three rotation angles ($\theta_x$, $\theta_y$, $\theta_z$). The two-dimensional coordinate system ($o_p x_p y_p$) is the imaging plane coordinate system, and the patient position is described by six parameters: two in-plane translations ($x_p$, $y_p$) and an in-plane rotation angle $\theta_z$ in the two-dimensional coordinate, and one out-of-plane translation z and two out-of-plane rotation angles ($\theta_x$, $\theta_y$) in the three-dimensional patient coordinate. There is a direct correspondence between the out-of-plane translation z and the three rotation angles ($\theta_x$, $\theta_y$, $\theta_z$) between the three-dimensional patient coordinate system and the two-dimensional coordinate system, and the two in-plane translations satisfy the following expressions: $x_p=ax$, $y_p=ay$, where the magnification factor $$a = \frac{|SO_p|}{|SO|},$$

$|SO_p|$ represents the distance from the center of the third ray source to the center of the imaging plane, and $|SO|$ represents the distance from the center of the third ray source to the center of the patient. During image registration, six parameter values ($x_p$, $y_p$, z, $\theta_x$, $\theta_y$, $\theta_z$) in the imaging plane coordinate system before registration are determined, and the six parameters (x, y, z, $\theta_x$, $\theta_y$, $\theta_z$) representing the patient position change in the patient coordinate system are determined by the six parameter values ($x_p$, $y_p$, z, $\theta_x$, $\theta_y$, $\theta_z$) in the imaging plane coordinate system; according to the six-dimensional patient positioning deviation calculated by registration, the treatment couch is controlled to make corrections, and radiotherapy is performed after the position of the patient meets clinical requirements.

When the three-sequence image-guided positioning system switches from the high-level treatment center 8 to the low-level treatment center 7, the treatment couch needs to drop by a distance of $h_2-h_1$. While the treatment couch is controlled to descend, the position change $\Delta d$ of the infrared marking point preset on the treatment couch can be monitored by the respiratory motion tracking system 4 to meet the following requirement: $\Delta d=h_2-h_1$, so as to ensure accurate switching from the high-level treatment center 8 to the low-level treatment center 7.

When in use, a computed tomography (CT) or magnetic resonance imaging (MRI) diagnostic image of a patient is input into a treatment planning system, a tumor target volume and critical organs are delineated, treatment nodes are selected from the fully-spherical treatment space, treatment dose distribution and dose allocation to each treatment node are calculated, and a treatment plan is developed. Treatment path is planned for the treatment nodes from the treatment space of the low-level treatment center and the treatment space of the high-level treatment center, and the image-guided positioning system performs image-guided positioning verification on the patient on the treatment couch, detects the patient's position deviation, and the multi-degree-of-freedom treatment couch automatically corrects the patient's position deviation. The multi-degree-of-freedom robot carrying the accelerator, reaches the treatment nodes on the treatment sphere, and then according to the treatment path planned by the treatment plan, the multi-degree-of-freedom robot carrying the accelerator, completes beam projection on multiple treatment nodes corresponding to the treatment space of the low-level treatment center, and is then switched to the high-level treatment center, and completes beam projection on multiple treatment nodes corresponding to the treatment space of the high-level treatment center.

In order to illustrate the effectiveness of the method proposed in this application, the above-mentioned technical solution of the present application is described below through embodiments.

Figure 6:
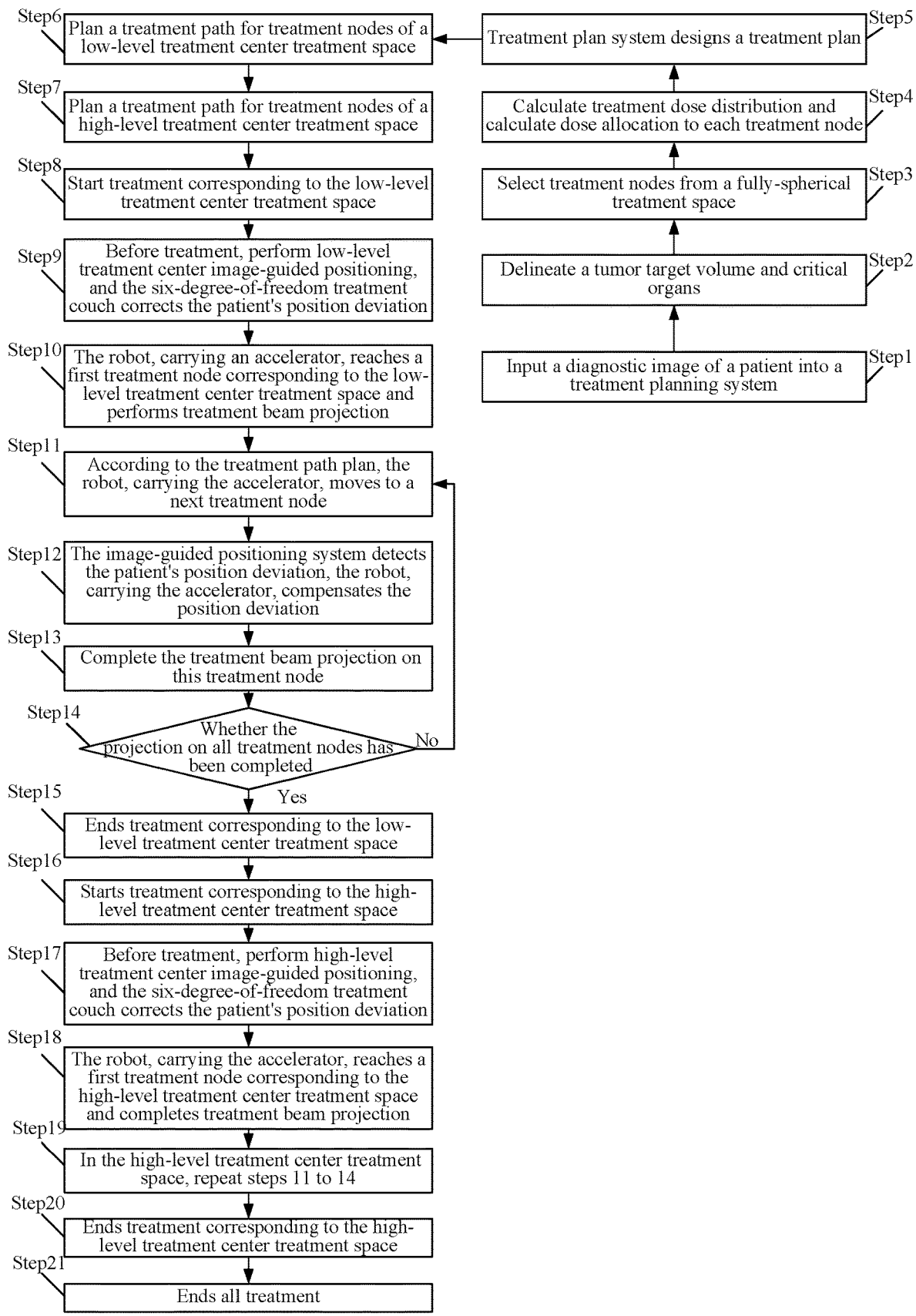
FIG. 6 is a treatment flowchart of the radiotherapy device according to the present application.

The treatment process of the radiotherapy system based on multi-isocenter is shown in FIG. 6, including the following steps: 1 to 21.

In step 1, in the treatment planning stage, a CT or MRI diagnostic image of a patient is input into a treatment planning system.

In step 2, a tumor target volume and critical organs are delineated.

In step 3, treatment nodes are selected from the fully-spherical treatment space.

In step 4, treatment dose distribution and dose allocation to each treatment node are calculated.

In step 5, a treatment plan is developed.

In steps 6 and 7, before treatment, the treatment path is planned for the treatment nodes of the treatment space of the low-level treatment center and the treatment nodes of the treatment space of the high-level treatment center.

In steps 8 and 9, the treatment corresponding to the treatment space of the low-level treatment center is started, the image-guided positioning system performs image-guided positioning verification on the patient on the treatment couch, detects the patient's position deviation, and the six-degree-of-freedom treatment couch automatically corrects the patient's position deviation.

In steps 10 to 13, in the treatment, the six-degree-of-freedom robot, carrying the accelerator, reaches a designated treatment node on the treatment sphere for treatment beam projection, and then according to the treatment path planned by the treatment plan, the six-degree-of-freedom robot, carrying the accelerator, completes beam projection on multiple treatment nodes corresponding to the treatment space of the low-level treatment center.

In step 14, it is determined whether the projection on all treatment nodes corresponding to the treatment space of the low-level treatment center has been completed, and if so, the process proceeds to step 15; and if not, the process returns to continue to perform steps 10 to 13.

In steps 15 to 19, the process is switched to the high-level treatment center, the image-guided positioning system performs image-guided positioning verification on the patient on the treatment couch, detects the patient's position deviation, and the six-degree-of-freedom treatment couch corrects automatically the patient's position deviation; the six-degree-of-freedom robot, carrying the accelerator, reaches a designated treatment node on the treatment sphere for treatment beam projection, and then according to the treatment path planned by the treatment plan, the six-degree-of-freedom robot, carrying the accelerator, completes beam projection on multiple treatment nodes corresponding to the treatment space of the high-level treatment center; and it is determined whether the projection on all treatment nodes corresponding to the treatment space of the high-level treatment center has been completed, and if so, the process proceeds to step 20; and if not, the process returns to continue to perform steps 15 to 19.

In step 20, the beam projection of the multiple treatment nodes corresponding to the treatment space of the high-level treatment center is completed and the treatment corresponding to the treatment space of the high-level treatment center is ended.

In step 21: all treatments are ended.

In the whole treatment process, for static target volumes such as the head, neck and spine which has no motion caused by breathing, the image-guided positioning system continuously detects the position deviation of the patient, and the six-degree-of-freedom robot correspondingly corrects the beam position on each treatment node to compensate for the position deviation of the patient; and for target volumes such as the thorax and the abdomen which has a motion caused by breathing, the breathing motion tracking system 4 tracks the breathing motion of the target volume in real time, and the six-degree-of-freedom robot drives the accelerator to continuously adjust the treatment beam to compensate for the motion of the target volume, so that motion tracking treatment is achieved.

Embodiment One

Figure 8A:
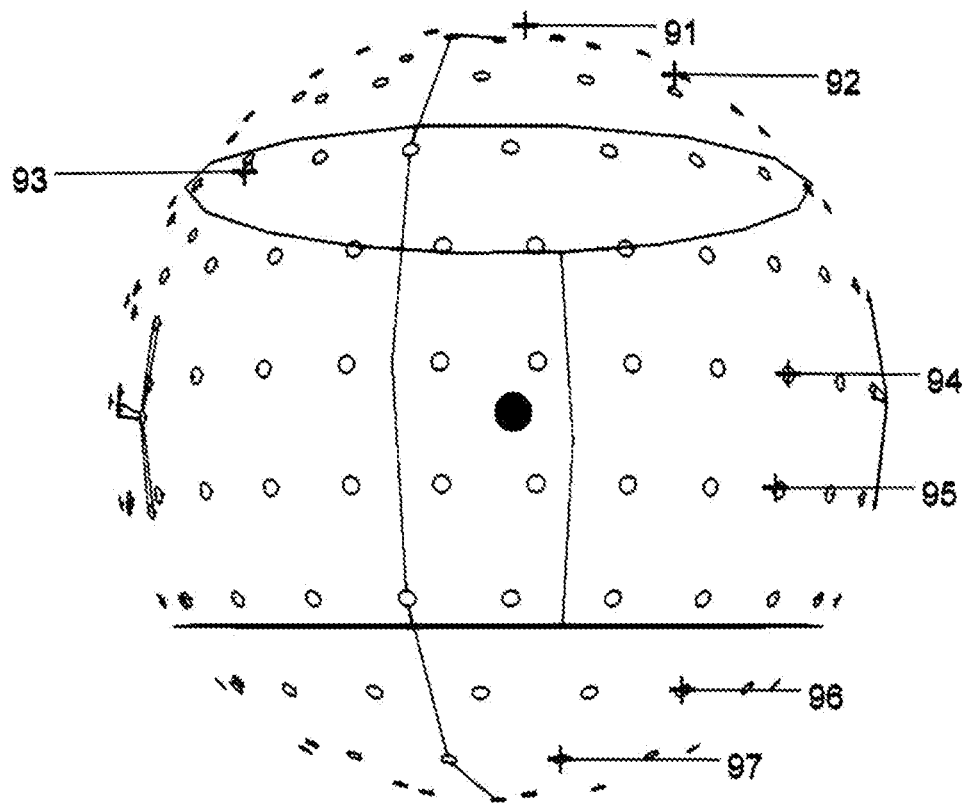
FIG. 8A is a schematic diagram showing fully-spherical treatment nodes of the radiotherapy device adopting a combined mode of the high-level treatment center treatment mode and low-level treatment center treatment mode according to the present application.

A treatment example adopting a combined treatment mode of a high-level treatment center treatment mode and a low-level treatment center treatment mode requires radiotherapy to be performed both above the patient and on the dorsum of the patient. It is assumed that a total of seven treatment nodes (the number of treatment nodes in a practical case may be several tens or more, and only seven treatment nodes are illustrated here) exist, as shown in FIG. 8A. Treatment node 91, treatment node 92, treatment node 93, treatment node 94 and treatment node 95 are for treatment in the low-level treatment center mode, and treatment node 96 and treatment node 97 are for treatment in the high-level treatment center mode. Treatment node 94 and the treatment node 95 are located in both the treatment space of the low-level treatment center and the treatment space of the high-level treatment center, and the combined mode of the high-level treatment center mode and the low-level treatment center mode is adopted for treatment in this embodiment.

Figure 8B:
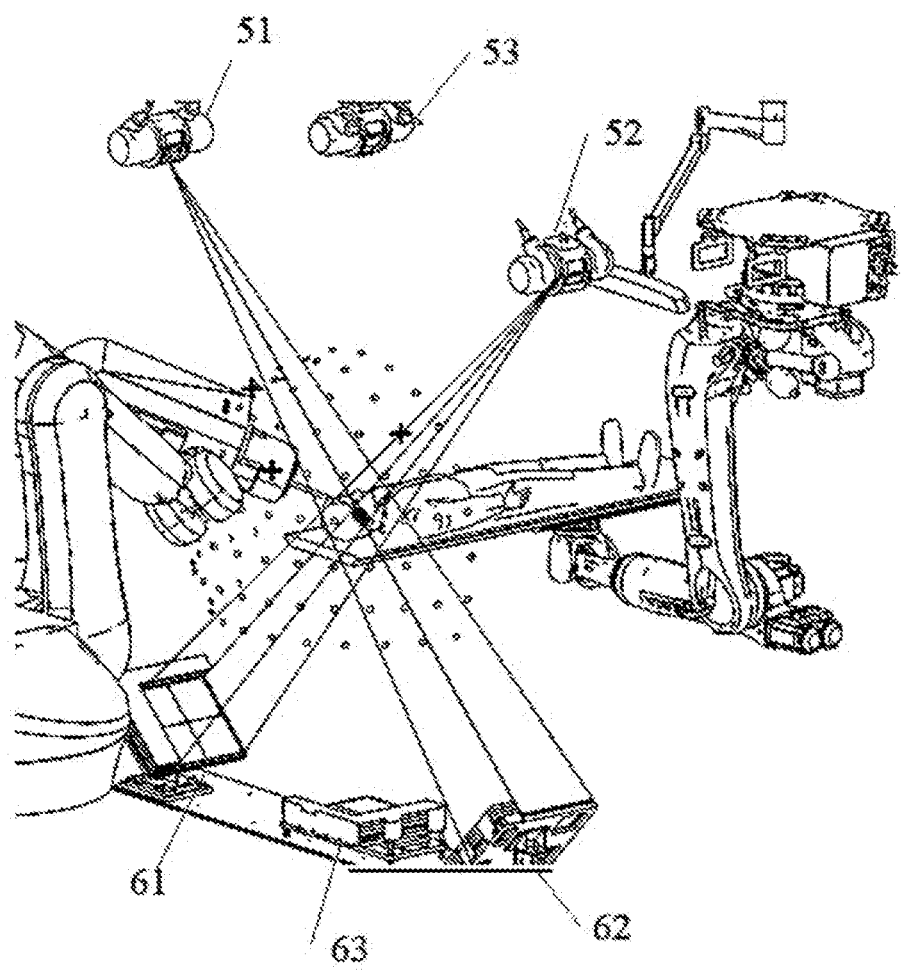
FIG. 8B is a schematic diagram showing treatment performed by the radiotherapy device adopting the combined mode of the high-level treatment center treatment mode and low-level treatment center treatment mode according to the present application.
Figure 8C:
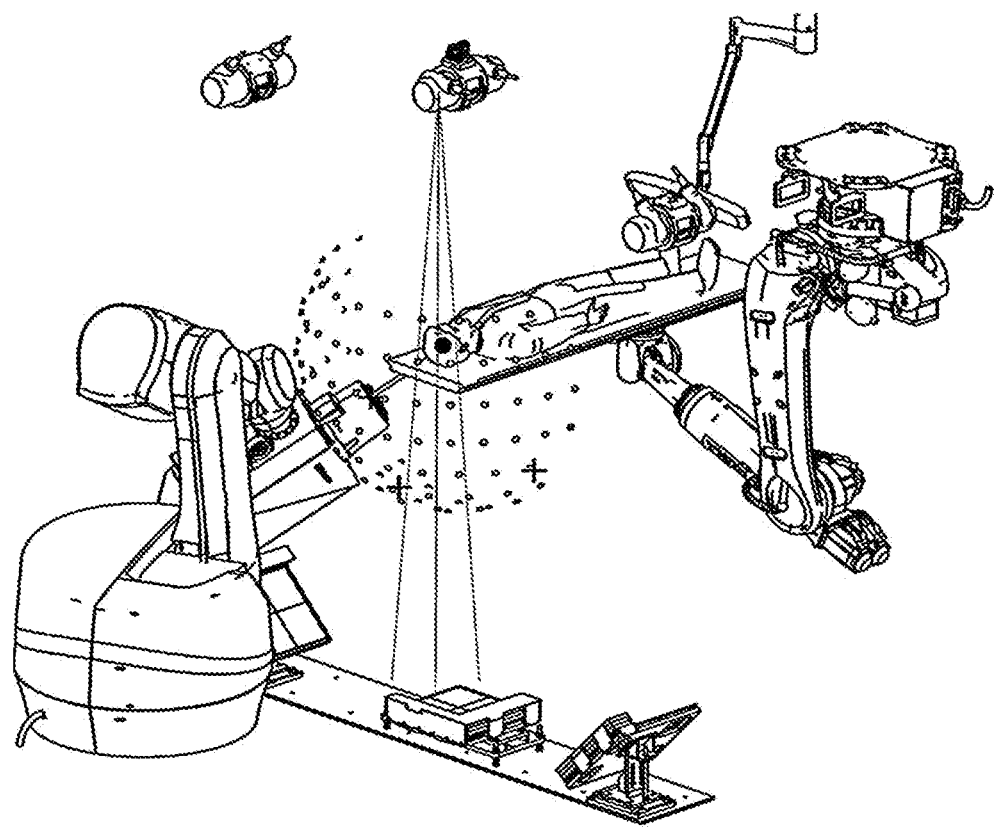
FIG. 8C is a schematic diagram showing another treatment performed by the radiotherapy device adopting the combined mode of the high-level treatment center treatment mode and low-level treatment center treatment mode according to the present application.

As shown in FIG. 8B to FIG. 8C, low-level treatment center image-guided positioning is performed according to the treatment path planned by the treatment plan, where di is 1780 mm, $d_{12}$ is 1850 mm, $d_{21}$ is 1800 mm, $d_{22}$ is 1450 mm, $h_1$ is 970 mm, $h_2$ is 1400 mm, a is 45°, $H_1$ is 2278 mm, and $H_2$ is 2770 mm. The six-degree-of-freedom robot, carrying the accelerator, reaches designated treatment node 91, designated treatment node 92, designated treatment node 93, designated treatment node 94 and designated treatment node 95 on the treatment sphere, sequentially, performs treatment beam projection and completes treatment corresponding to the treatment space of the low-level treatment center. The left and right sequence image-guided positioning is used by default during low-focus treatment. For the treatment node 93, the middle and right sequence image-guided positioning may be chosen since the treatment head robot blocks the left sequence imaging. Then, the six-degree-of-freedom robot is switched to the high-level treatment center image-guided positioning, the six-degree-of-freedom robot, carrying the accelerator, reaches designated treatment node 96 and designated treatment node 97 on the treatment sphere sequentially, performs treatment beam projection and completes treatment corresponding to the treatment space of the high-level treatment center.

Embodiment Two

Figure 9A:
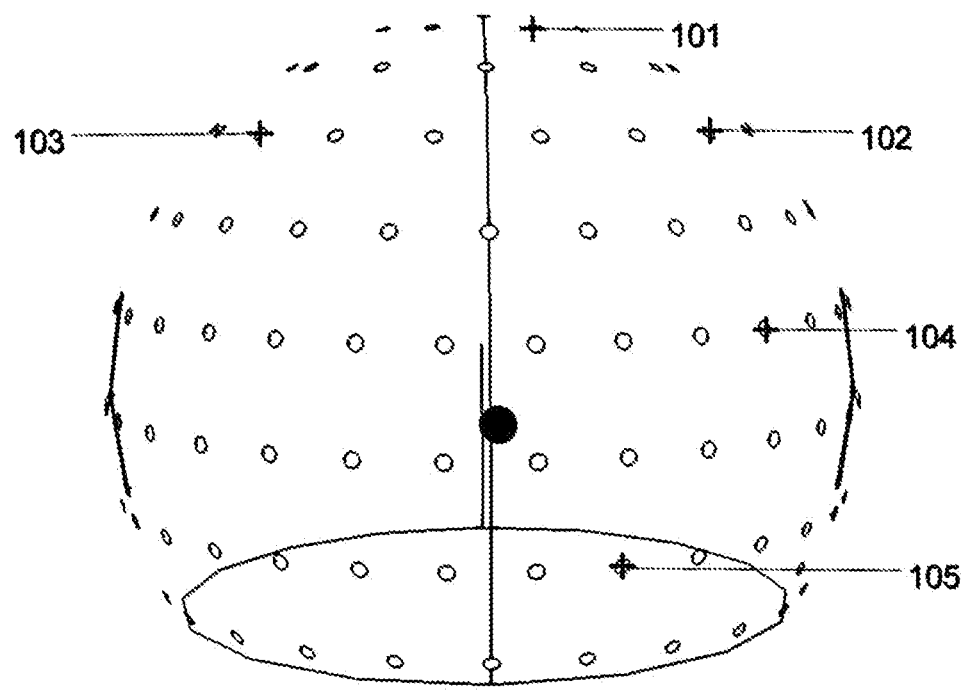
FIG. 9A is a schematic diagram showing fully-spherical treatment nodes of the radiotherapy device adopting the low-level treatment center treatment mode according to the present application.

A treatment example adopting the low-level treatment center treatment mode requires radiotherapy to be performed above and on the two sides of the patient. It is assumed that a total of five treatment nodes (the number of treatment nodes in a practical case may be several tens or more, and only five treatment nodes are illustrated here) exist, a treatment node 101, treatment node 102, treatment node 103, treatment node 104 and treatment node 105 are all for treatment in the low-level treatment center mode, as shown in FIG. 9A.

Figure 9B:
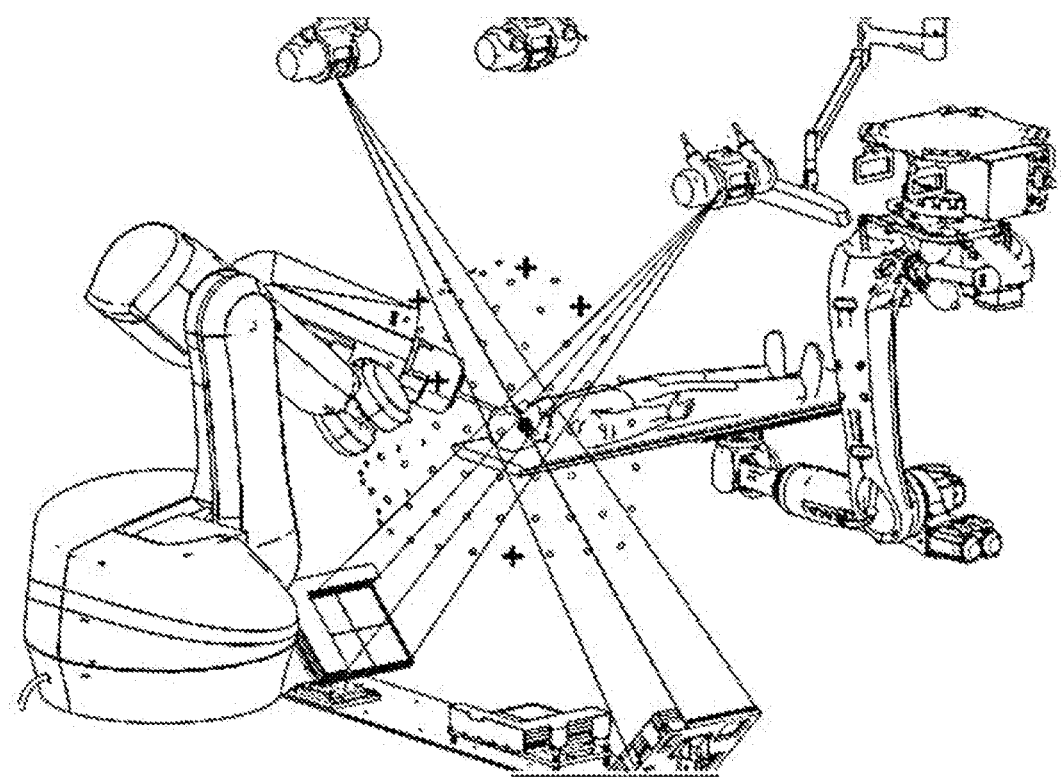
FIG. 9B is a schematic diagram showing treatment performed by the radiotherapy device adopting the low-level treatment center treatment mode according to the present application.

As shown in FIG. 9B, low-level treatment center image-guided positioning is performed according to the treatment path planned by the treatment plan, where $d_{11}$ is 1780 mm, $d_{12}$ is 1850 mm, $d_{21}$ is 1800 mm, $d_{22}$ is 1450 mm, $h_1$ is 970 mm, $h_2$ is 1400 mm, $\alpha$ is 45°, $H_1$ is 2278 .mm, and $H_2$ is 2770 mm. The six-degree-of-freedom robot, carrying the accelerator, reaches the designated treatment node 101, designated treatment node 102, designated treatment node 103, designated treatment node 104 and designated treatment node 105 on the treatment sphere, sequentially, performs treatment beam projection and completes treatment corresponding to the treatment space of the low-level treatment center. The left and right sequence imaging is adopted by default for positioning in the low-level treatment center treatment mode. For the treatment node 102, since the treatment head robot blocks the right sequence imaging, the left and middle sequence imaging may be chosen for positioning; and for the treatment node 103, since the treatment head robot blocks the left sequence imaging, the middle and right sequence imaging may be chosen for positioning.

Embodiment Three

Figure 10A:
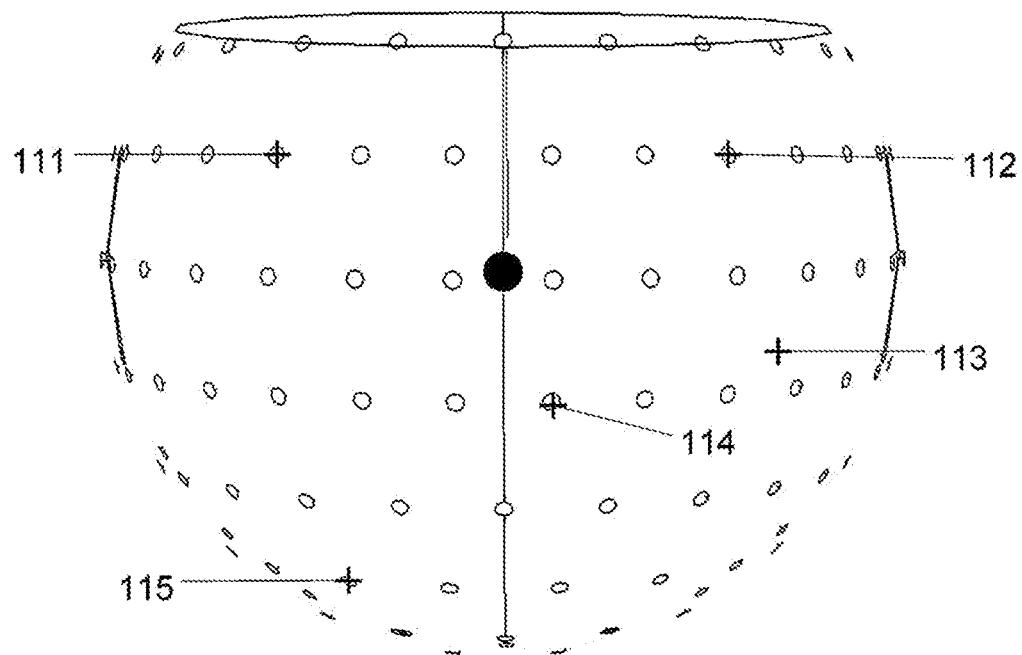
FIG. 10A is a schematic diagram showing fully-spherical treatment nodes of the radiotherapy device adopting the high-level treatment center treatment mode according to the present application.

A treatment example adopting a high-level treatment center treatment mode requires radiotherapy to be performed below and on two sides of the patient. It is assumed that a total of five treatment nodes (the number of treatment nodes in a practical case may be several tens or more, and only five treatment nodes are illustrated here) exist, a treatment node 111, treatment node 112, treatment node 113, treatment node 114 and treatment node 115 are all for treatment in the high-level treatment center treatment mode, as shown in FIG. 10A.

Figure 10B:
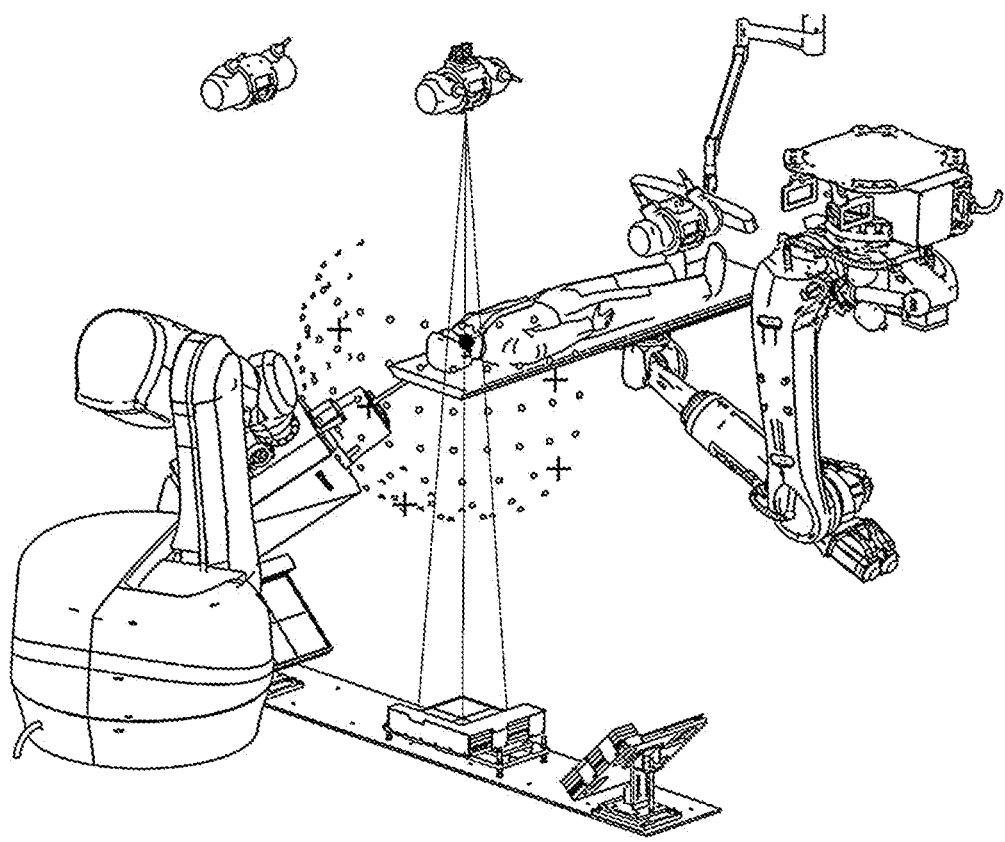
FIG. 10B is a schematic diagram showing treatment performed by the radiotherapy device adopting the high-level treatment center treatment mode according to the present application.

As shown in FIG. 10B, high-level treatment center image-guided positioning is performed according to the treatment path planned by the treatment plan, where $d_{21}$ is 1800 mm, $d_{22}$ is 1450 mm, $h_2$ is 1400 mm, and $H_2$ is 2770 mm. The six-degree-of-freedom robot, carrying the accelerator, reaches the designated treatment node 111, designated treatment node 112, designated treatment node 113, designated treatment node 114 and designated treatment node 115 on the treatment sphere sequentially, performs middle single-sequence imaging for positioning, performs treatment beam projection and completes treatment corresponding to the treatment space of the high-level treatment center.

With the present application, at least the following beneficial effects can be achieved:

(1) For the treatment space of the high-level treatment center, beams are projected on the target volumes near the dorsum, such as the spinal target volume and the chest and abdominal target volumes near the dorsum, so that the patient can receive effective treatment in a normal supine lying position.

(2) For the fully-spherical treatment space combining the treatment space of the low-level treatment center and the treatment space of the high-level treatment center, multiple target volumes are enabled to receive more treatment beam projection, obtain a more optimized and effective treatment dose distribution, and achieve better treatment effects.

(3) During treatment corresponding to the low-level treatment center, according to the different positions of the treatment head mechanical arm and the imaging path blockage situations, it is possible to use only two imaging sequences that do not block any imaging path to perform image-guided positioning throughout the treatment process, thereby achieving better treatment effects.

(4) The switching between the low-level treatment center and the high-level treatment center is fast; during treatment corresponding to the high-level treatment center, the middle vertical single sequence image-guided positioning is adopted. Compared with the imaging by obliquely crossing, the vertical sequence imaging geometry is more similar to conventional physical examination digital radiography (DR) imaging, and can achieve better imaging quality and effects.

(5) The positions of the X-ray tube and the flat-panel detector are fixed. During the treatment, only the treatment couch needs to be adjusted to reach the low-level treatment center or the high-level treatment center, and there is no need to recalibrate the image-guided positioning systems.

What is claimed is:

1. A radiotherapy system based on multi-isocenter, comprising an accelerator and a three-sequence image-guided positioning system;

wherein the three-sequence image-guided positioning system comprises a plurality of low-level image-guided positioning systems corresponding to a low-level treatment center and a high-level image-guided positioning system corresponding to a high-level treatment center; and the high-level image-guided positioning system is arranged among the plurality of low-level image-guided positioning systems; and the low-level treatment center is located at an intersection of two beams generated by any two image-guided positioning systems of the plurality of low-level image-guided positioning systems and the high-level image-guided positioning system; a beam generated by the high-level image-guided positioning system passes through the high-level treatment center; and a plurality of treatment nodes with the low-level treatment center as a spherical center and a plurality of treatment nodes with the high-level treatment center as a spherical center respectively form a fully-spherical treatment space;

wherein the plurality of low-level image-guided positioning systems and the high-level image-guided positioning system each comprise a ray source and a ray detector the ray source and the ray detector of the plurality of low-level image-guided positioning systems produce two X-ray images on two projection planes respectively, and the ray source and the ray detector of the high-level image-guided positioning system produce one X-ray image on one projection plane; and wherein in the low-level treatment center, two unblocked beams are selected for image-guided positioning, and in the high-level treatment center, only a beam from the high-level image-guided positioning system is used for image-guided positioning.

2. The radiotherapy system according to claim 1, further comprising a multi-degree-of-freedom robot; wherein the accelerator is arranged on the multi-degree-of-freedom robot; and the multi-degree-of-freedom robot carrying the accelerator forms at least one of the following: a treatment space of the low-level treatment center above and on both sides of a patient around the low-level treatment center, or a treatment space of the high-level treatment center below and on both sides of a patient around the high-level treatment center.

3. The radiotherapy system according to claim 1, wherein the low-level treatment center and the high-level treatment center meet the following conditions:

$$3000 \text{ mm} \leq d_{11}+d_{12} \leq 3800 \text{ mm} \tag{1}$$

$$0.69 \leq h_1/d_{11} \leq 0.72 \tag{2}$$

$$3000 \text{ mm} \leq d_{21}+d_{22} \leq 3500 \text{ mm} \tag{3}$$

$$0.72 \leq h_2/d_{21} \leq 0.98 \tag{4}$$

$$0.42 \leq (h_2-h_1)/h_1 \leq 0.56 \tag{5}$$

wherein, $d_{11}$ is a distance from the low-level treatment center to an imaging center of a ray detector corresponding to the low-level treatment center; $d_{12}$ is a distance from the low-level treatment center to a ray source of a low-level image-guided positioning system; $d_{21}$ is a distance from the high-level treatment center to the ray detector of the high-level image-guided positioning system; $d_{22}$ is a distance from the high-level treatment center to the ray source of the high-level image-guided positioning system; $h_1$ is a height of the low-level treatment center from a ground; and $h_2$ is a height of the high-level treatment center from the ground.

4. The radiotherapy system according to claim 3, wherein a distance $H_1$ between the ray source of the low-level image-guided positioning system and the ground is $H_1=h_1+\cos(\alpha)d_{12}$, wherein $\alpha$ is an included angle between a beam of the low-level image-guided positioning system and a vertical plane with respect to the ground.

5. The radiotherapy system according to claim 3, wherein a distance $H_2$ from the ray source of the high-level image-guided positioning system to the ground is $H_2=h_2+d_{22}$.

6. The radiotherapy system according to claim 3, wherein an included angle between a beam of the low-level image-guided positioning system and a vertical plane with respect to the ground is $\alpha$, $\alpha=\arccos(d_{11}/(h_1+d))$, wherein d is a distance from a ray detector of a low-level image-guided positioning system to the ground.

7. The radiotherapy system according to claim 1, wherein the ray source is an X-ray tube; and the ray detector is a flat-panel detector.

8. The radiotherapy system according to claim 1, further comprising an adjustment and calibration device, wherein the ray detector is connected to the adjustment and calibration device.

9. The radiotherapy system according to claim 8, wherein the adjustment and calibration device comprises a height adjustment mechanism, a plane longitudinal adjustment mechanism, and a plane lateral adjustment mechanism.

\* \* \* \* \*